United States Patent [19]

Morris et al.

[11] 4,170,650
[45] Oct. 9, 1979

[54] OXOPIPERAZINIUM SALTS, THEIR PREPARATION AND THEIR USE

[75] Inventors: Nancy J. Morris; John W. Bozzelli, both of Midland, Mich.

[73] Assignee: The Dow Chemical Company, Midland, Mich.

[21] Appl. No.: 908,192

[22] Filed: May 22, 1978

[51] Int. Cl.² ............... C07D 241/08; A61K 31/495; A01N 9/22
[52] U.S. Cl. .................... 424/250; 544/384
[58] Field of Search .................. 544/384; 424/250

[56] References Cited

U.S. PATENT DOCUMENTS

| 2,653,153 | 9/1953 | Benneville | 544/384 |
| 3,072,658 | 1/1963 | Faneher | 544/384 |
| 3,365,453 | 1/1968 | Archer | 544/384 |
| 3,390,139 | 6/1968 | Benneville | 544/384 |

OTHER PUBLICATIONS

Melandri et al., Chem. Abs. 62, 10435c (1965).

Durand et al., Chem. Abs. 64, 3532 (1964).

*Primary Examiner*—Mark L. Berch
*Attorney, Agent, or Firm*—G. R. Plotecher

[57] ABSTRACT

Quaternary ammonium salts of the formula

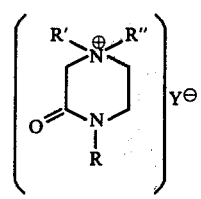

(I)

where R, R' and R" are typically individually alkyl or inertly-substituted alkyl radicals and Y⊖ is a neutralizing anion, are readily prepared by quaternizing the nonamide ring nitrogen of an N-alkyl piperazinone. These quaternary ammonium salts demonstrate biological activity.

3 Claims, No Drawings

OXOPIPERAZINIUM SALTS, THEIR PREPARATION AND THEIR USE

BACKGROUND OF THE INVENTION

1. Field of the Invention

This invention relates to novel quaternary ammonium salts, a process for their preparation and their use as biologically active agents.

2. Description of the Prior Art

Quaternary ammonium compounds as a class have long been known in the art and vary in size and complexity from tetramethyl ammonium salts to polymeric compounds. These salts have a wide variety of utility which include surfactants, germicides, thickening agents, etc.

SUMMARY OF THE INVENTION

This invention provides a new subclass of quaternary ammonium salts. These salts demonstrate biological activity and are of the formula

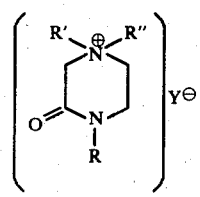

(I)

where
- R is hydrogen or R';
- R' is a $C_1$–$C_5$ alkyl radical;
- R'' is an aliphatic, alicyclic, aryl or an inertly-substituted aliphatic, alicyclic or aryl radical; and
- $Y^\ominus$ is a neutralizing anion.

The aliphatic and alicyclic radicals of R'' are typically of 1 to about 30 carbon atoms, preferably of 8 to about 20 carbon atoms, and the aryl radical is typically and preferably phenyl. The quaternary ammonium salts of this invention are readily prepared by quaternizing the nonamide ring nitrogen of an N-alkyl piperazinone. "Nonamide ring nitrogen" here refers to the ring nitrogen not adjacent to the ring carbonyl carbon of the piperazinone. "N-alkyl" here means the nonamide ring nitrogen of the piperazinone bearing an alkyl substituent.

DETAILED DESCRIPTION OF THE INVENTION

N-alkyl piperazinones (II) are known compounds and can be prepared by reacting a carbonyl compound, hydrogen cyanide and an ethylene diamine (U.S. Pat. Nos. 2,649,450 and 2,700,668).

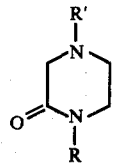

(II)

Here, as elsewhere herein, both R and R' are preferably methyl. Moreover, the ring carbons (except for the carbonyl carbon) of II and the corresponding carbons of the other formulae herein can bear a $C_1$–$C_4$ alkyl radical. Preferably, these ring carbons are unsubstituted.

The preparation of the quaternary ammonium salts of this invention is an esentially one-step method, i.e., the quaternization of II.

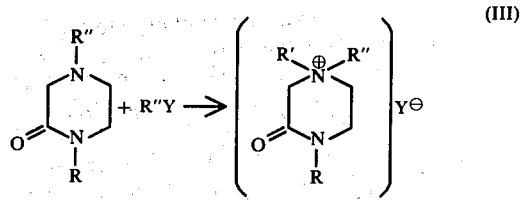

(III)

The quaternizing agent,

R''Y  (IV)

can be any compound that will both quaternize the original ring nitrogen and provide a neutralizing anion ($Y^\ominus$) after the quaternization. R'' is as defined previously. The aryl radicals of R'' include: phenyl, biphenyl, naphthyl, anthracyl, phenanthracyl, etc. with phenyl the preferred aryl radical. These aryl radicals as well as the aliphatic and alicyclic radicals of R'', can bear one or more inert substituents, i.e., substituents that are essentially nonreactive with the products or reagents of process III. Typical inert substituents include: ether oxygen, carbonyl, other aliphatic, alicyclic or aryl radicals, aralkyl, amino, imino, cyano, etc. Preferably, R'' is an aliphatic, alicyclic or an inertly-substituted aliphatic or alicyclic radical of 8 to about 20 carbon atoms.

$Y^\ominus$ can be any suitable anion, such as halogen anion, e.g., fluoride, chloride, bromide, etc.; alkyl sulfate, e.g., methylsulfate, ethylsulfate, etc.; bisulfate; an organic anion, e.g., tosylate, acetate, etc.; and the like. Aliphatic and inertly-substituted aliphatic halides and sulfates are the preferred quaternizing agents. Representative quaternizing agents include: dimethyl sulfate, α-bromo-2,6-dichlorotoluene, 3-bromo-1,1-dichloropropene, 1,3-dichloropropene, α-bromo-4-nitrotoluene, octyl bromide, benzylchloride, methylethyl sulfate, tosyl chloride, bromobenzene, iodobenzene, etc.

The process of III is conducted under an inert atmosphere, such as nitrogen, and is usually conducted at a temperature of about 25° C. to about 150° C. and preferably at a temperature between about 40° C. and 60° C. Process III is exothermic and thus generates its own heat. For reasons of convenience, the temperature of III is maintained within the stated broad range, preferably within the stated narrow range, and is readily controlled by monitoring the rate of addition of one reagent to another, preferably by monitoring the rate of addition of the quaternizing agent to the piperazinone. Other control means, such as a cooling jacket, can also be used.

Process III can be conducted at any pressure but autogenous (usually atmospheric) pressure is preferred.

Process III can also be conducted either neat or in the presence of an inert solvent, but process III is preferably conducted in the presence of a solvent, preferably a polar solvent, such as tetrahydrofuran. Other suitable solvents include: hexane, cyclohexane, benzene, chloroform, carbon tetrachloride, etc.

Stoichiometric amounts of the respective reagents are required but preferably a slight excess of quaternizing agent is employed.

The final product, i.e., the quaternary ammonium salt, is typically a colored, crystalline or granular material, the color ranging from white to pink depending upon the quaternizing agent employed. The process of preparation is clean, efficient and facile. Product yield is essentially quantitative.

The quaternary ammonium salts of this invention are biologically active and are used in the same manner as known biologically active materials. "Biologically active" here means that the quaternary ammonium salts will inhibit the growth of one or more organisms, such as a bacteria, fungi, insect, plant, etc.

The following examples are illustrative embodiments of this invention. Unless indicated to the contrary, all parts and percentages are by weight.

SPECIFIC EMBODIMENTS

EXAMPLE 1

Piperazinium: 1,1,4-trimethyl-3-oxo-, Methylsulfate

N,N'-dimethylpiperazinone (25.2 g) dissolved in tetrahydrofuran (100 ml) was charged to a 3-neck, 250 ml flask equipped with a dropping funnel, water-cooled condenser and an air stirrer. Dimethyl sulfate (24.8 g) was slowly added dropwise with constant monitoring of the flask temperature. An immediate reaction was observed along with an exotherm between about 5° C. and about 40° C., the size of the exotherm depending upon the rate of addition of dimethyl sulfate. After the completion of the addition of the dimethyl sulfate, the reaction mixture was stirred for about an additional 2 hours. The product precipitated from solution as a slightly pink, powdery solid. The reaction flask was cooled, the product separated by filtration and subsequently washed with tetrahydrofuran, and then finally dried. The final product was identified by infrared, nuclear magnetic resonance and carbon, hydrogen and nitrogen elemental analysis. The product yield was essentially quantitative and the product was shown to be effective at 100 ppm in the control and killing of mouse trichostrongylid.

EXAMPLE 2

The procedure of Example 1 was repeated except that α-bromo-2,6-dichlorotoluene was substituted for the dimethyl sulfate. Piperazinium: 1-(2,6-dichlorophenyl)methyl)-1,4-dimethyl-3-oxo-, bromide was recovered in essentially quantitative yield. The product was shown to be effective at 400 ppm in the control and killing of beet army worm larvae.

Although this invention has been described in considerable detail with respect to the above examples, such detail is for the purpose of illustration only and is not to be construed as a limitation upon the invention. Many variations can be had without departing from the spirit of the invention or the scope of the appended claims.

What is claimed is:

1. Piperazinium: 1,1,4-trimethyl-3-oxo-, methylsulfate and piperazinium: 1-(2,6-dichlorophenyl)methyl)-1,4-dimethyl-3-oxo-, bromide.

2. The method for the control and killing of mouse trichostrongylid, the method comprising adminstering to the mouse trichostrongylid a control and killing amount of piperazinium: 1,1,4-trimethyl-3-oxo-, methylsulfate.

3. A method for the control and killing of beet army worm larvae, the method comprising administering to the larvae a control and killing amount of piperazinium: 1-(2,6-dichlorophenyl)methyl)-1,4-dimethyl-3-oxo-, bromide.

* * * * *